(12) United States Patent
Kamal et al.

(10) Patent No.: US 6,800,622 B1
(45) Date of Patent: Oct. 5, 2004

(54) PYRENE-LINKED PYRROLO[2,1-C][1,4] BENZODIAZEPINE HYBRIDS USEFUL AS ANTI-CANCER AGENTS

(75) Inventors: Ahmed Kamal, Hyderabad (IN); Ramesh Gujjar, Hyderabad (IN); Ramulu Poddutoori, Hyderabad (IN); Srinivas Olepu, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/396,129

(22) Filed: Mar. 25, 2003

(51) Int. Cl.[7] .................... C07D 487/00; A61K 31/55
(52) U.S. Cl. ...................... 514/220; 540/496
(58) Field of Search ............. 514/220; 540/496

(56) References Cited

PUBLICATIONS

Zhou et al. (J. Am. Chem. Soc. 2001, 123, 4865–4866).*

* cited by examiner

*Primary Examiner*—Bruck Kifle
(74) *Attorney, Agent, or Firm*—Ladas & Parry

(57) ABSTRACT

The present invention relates to a process for the preparation of novel pyrrolo [2,1-c][1,4]benzodiazepine hybrids useful as antitumour agents. This invention also relates to a process for the preparation of new pyrrolo[2,1-c][1,4] benzodiazepine hybrids as potential antitumour agents. More particularly, it provides a process for the preparation of 7-methoxy-8-[N-(1"-pyrenyl)-alkane-3'-carboxamide]-oxy-(11aS)-1,2,3,11a-tetraydro 5H-pyrrolo[2,1-c][1,4] benzodiazepine-5-one, with aliphatic chain length variation of these compounds and it also describes the DNA binding, anticancer (antitumour) activity. The structural formula of this novel pyrrolo[2,1-c][1,4]benzodiazepine is given below:

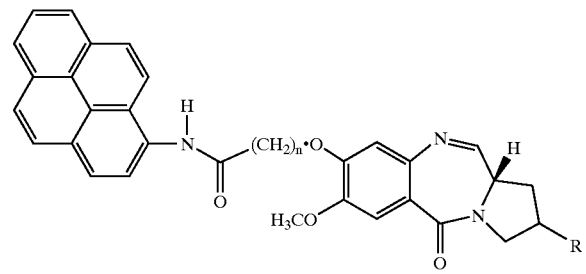

n = 1–4
R = H, OH

13 Claims, No Drawings

PYRENE-LINKED PYRROLO[2,1-C][1,4] BENZODIAZEPINE HYBRIDS USEFUL AS ANTI-CANCER AGENTS

FIELD OF THE INVENTION

The present invention relates to a process for the preparation of novel pyrrolo [2,1-c][1,4]benzodiazepine hybrids useful as potential antitumour agents. This invention also relates to a process for the preparation of new pyrrolo[2,1-c][1,4]benzodiazepine hybrids as potential antitumour agents. More particularly, it provides a process for the preparation of 7-methoxy-8-[N-(1"-pyrenyl)-alkane-3'-carboxamide]-oxy-(11aS)-1,2,3,11a-tetraydro 5H-pyrrolo [2,1-c][1,4]benzodiazepine-5-one, with aliphatic chain length variation of these compounds and it also describes the DNA binding, anticancer (antitumour) activity. The structural formula of this novel pyrrolo[2,1-c][1,4] benzodiazepine is given below:

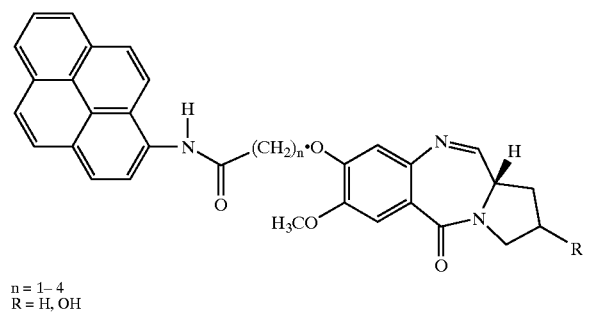

n = 1–4
R = H, OH

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepine PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Naganawa, H.; Miyamoto, M.; Takeuchi, T.; and Unezawa, *H. J. Antibiot.*, 1980, 33, 665.; Kohn, K. W. and Speous, C. L. *J. Mol. Biol.*, 1970, 51, 551.; Hurley, L. H.; Gairpla, C. and Zmijewski, M. *Biochem. Biophys. Acta.*, 1977, 475, 521.; Kaplan, D. J. and Hurley, L. H. *Biochmestry*, 1951, 20, 7572). The molecules have a right-handed twist, which allows them to follow the curvature of the minor groove of B-form double-stranded DNA spanning three base pairs. Recently, PBD dimers have been developed that comprises two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A recent development has been the linking of two PBD units through their C-8 positions to give bisfunctional alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.*, 1996, 61, 8141).

Recently, a noncross-linking mixed imine-amide PBD dimers have been synthesized that have significant DNA binding ability and potent anti tumour activity. (Kamal, A.; Ramesh, G.; Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

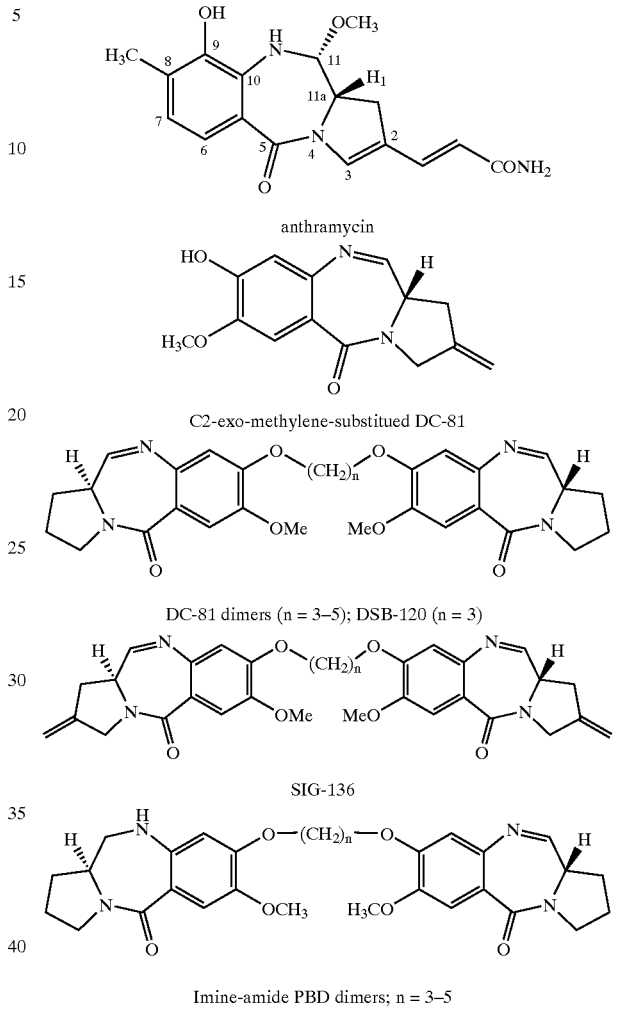

Naturally occurring pyrrolo[2,1-c][1,4]benzodiazepines belong to a group of antitumour antibiotics derived from Streptomyces species. Recently, there is much impetus for the PBD systems as they can recognize and bind to specific sequence of DNA. Examples of naturally occurring PBD's include anthramycin, DC-81, tomaymycin, sibiromycin and neothramycin. However, the clinical efficacy for these antibiotics is hindered by several limitations, such as poor water solubility, cardiotoxicity, development of drug resistance and metabolic inactivation.

OBJECTS IF THE INVENTION

The main object of the present invention is to provide new pyrrolo[2,1-c][1,4]-benzodiazepine hybrids useful as antitumour agents.

Another objective of the present invention is to provide a process for the preparation of novel pyrrolo[2,1-c][1,4]-benzodiazepine hybrids useful as antitumour agents.

SUMMARY OF THE INVENTION

Accordingly the present invention provides a process for the preparation of a novel pyrrolo[2,1-c][1,4] benzodiazepine hybrids of formula V wherein R=H, OH and n is 1–4

FORMULA V

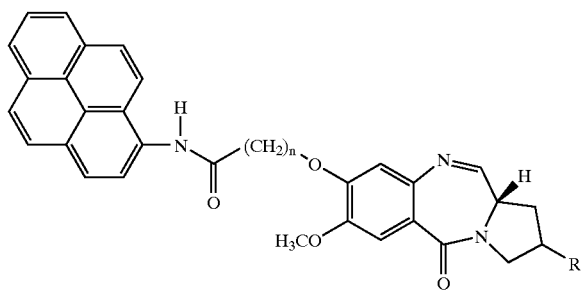

n = 1–4
R = H, OH

Accordingly the present process provides a process for preparation of pyrrolo[2,1-c][1,4]benzodiazepine hybrids of formula V

FORMULA V

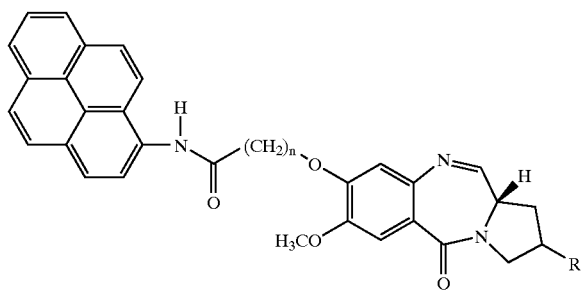

n = 1–4
R = H, OH which comprise reacting pyrene amine of formula I

I

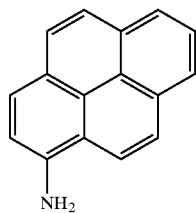

with (2S)-N-{4-[(3'-carboxyalkyl)oxy]-5-methoxy-2-nitrobenzoyl}pyrrolidine-2-carboxaldehyde diethyl thioacetal of formula II where R is as stated above

II

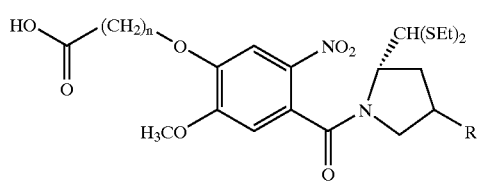

in the presence of isobutyl chloroformate, bases like triethyl amine, DBU in presence of organic solvents up to refluxing for a period of 24 h isolating (2S)-N-{4-[N-(1"-pyrenyl)-alkane-3'-carboxamide]-oxy-5-methoxy-2-nitrobenzoyl}pyrrolidine-2-carboxaldehyde diethyl thioacetal III where n is 1–4 and R is as stated above by conventional methods,

III

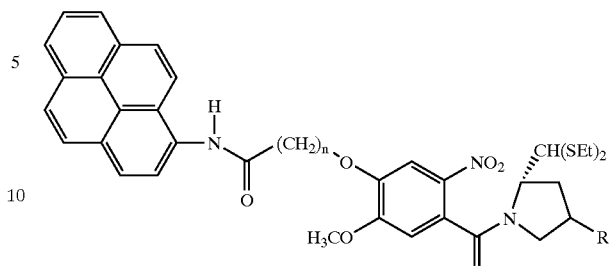

reducing the above nitro compounds of formula III with $SnCl_2.2H_2O$ in presence of organic solvent up to a reflux temperature, isolating the (2S)-N-{4-[N-(1"-pyrenyl)-alkane-3'-carboxamide]-oxy-5-methoxy-2-aminobenzoyl}pyrrolidine-2-carboxaldehyde diethyl thioacetal of formula IV where n is 1–4 and R is as stated above by known methods,

IV

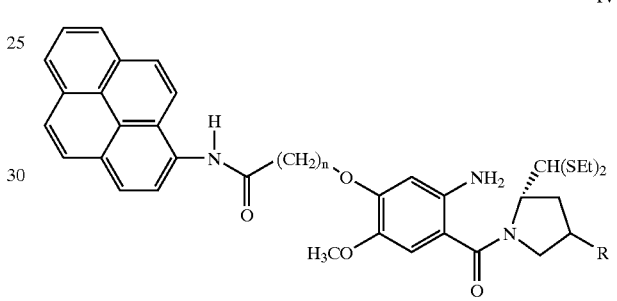

reacting the above said amino compound of formula IV with known deprotecting agents in a conventional manner to give novel pyrrolo[2,1-c][1,4]benzodiazepine hybrids of formula V wherein n and R are as stated above.

DETAILED DESCRIPTION OF THE INVENTION

The precursors, pyrene amine of formula I (Banik, B. K.; Becker, F. F. *Bioorg. Med. Chem.* 2001, 9, 593) and (2S)-N-{4-[(3'-carboxyalkyl)oxy]-5-methoxy-2-nitrobenzoyl}pyrrolidine-2-carboxaldehyde diethyl thioacetal of formula II (Baraldi, P. G.; Balboni, G.; Cacciari, B.; Guiotto, A.; Manfredini, S.; Romagnoli, R.; Spalluto, G.; Thurston, D. E.; Howard, P. W.; Bianchi, N.; Rutigiiano, C.; Mischiati, C. and Gambari, R. *J. Med. Chem.* 1999, 42, 5131.; Reddy, B. S. P.; Damayanthi, Y.; Reddy, B. S. N.; Lown, W. *J. Anti-Cancer Drug Design* 2000, 15, 225) have been prepared by literature methods.

These new analogues of pyrrolo[2,1-c][1,4] benzodiazepine hybrids linked at C-8 position have shown promising DNA binding activity and efficient anticancer activity in various cell lines. The molecules synthesized are of immense biological significance with potential sequence selective DNA-binding property. This resulted in design and synthesis of now congeners as illustrated in Scheme-1, which comprise:

1. The ether linkage at C-8 position of DC-81 intermediates with pyrene ring moiety.
2. Refluxing the reaction mixture for 24–48 h.
3. Synthesis of C-8 linked PBD antitumour antibiotic hybrid imines.

4. Purification by column chromatography using different solvents like ethyl acetate, hexane, dichloromethane and methanol.

SCHEME I

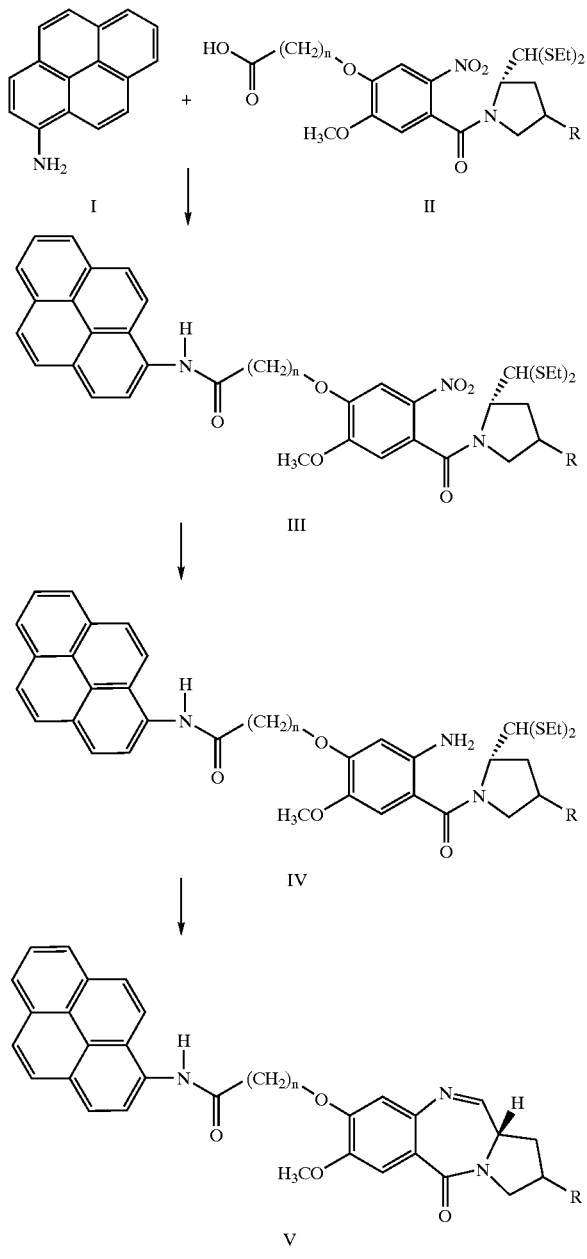

n = 1–4
R = H, OH

Some representative compounds of formula V present invention are given below
1. 7-Methoxy-8-[N-(1"-pyrenyl)-methane-1'-carboxamide]-oxy-(11aS) 1,2,3,11a tetrahydro-5H-pyrrolo[2,1-c][1,4]benzodiazepin-5-one
2. 7-Methoxy-8-[N-(1"-pyrenyl)-methane-1'-carboxamide]-oxy-(4R)-hydroxy (11aS) 1,2,3,11a tetrahydro-5H-pyrrolo[2,1-c][1,4]benzodiazepin-5-one
3. 7-Methoxy-8-[N-(1"-pyrenyl)-ethane-2'-carboxamide]-oxy-(11aS) 1,2,3,11a tetrahydro-5H-pyrrolo[2,1-c][1,4]benzodiazepin-5-one
4. 7-Methoxy-8-[N-(1"-pyrenyl)-ethane-2'-carboxamide]-oxy-(4R)-hydroxy (11aS) 1,2,3,11a tetrahydro-5H-pyrrolo[2,1-c][1,4]benzodiazepin-5-one
5. 7-Methoxy-8-[N-(1"-pyrenyl)-propane-3'-carboxamide]-oxy-(11aS)-1,2,3,11a tetra-hydro-5H-pyrrolo[2,1-c][1,4]benzodiazepin-5-one
6. 7-Methoxy-8-[N-(1"-pyrenyl)-propane-3'-carboxamide]-oxy-(4R)-hydroxy (11aS)-1,2,3,11a-tetra-hydro-5H-pyrrolo[2,1-c][1,4]benzodiazepin-5-one
7. 7-Methoxy-8-[N-(1"-pyrenyl)-butane-4'-carboxamide]-oxy-(11aS)-1,2,3,11a-tetra-hydro-5H-pyrrolo[2,1-c][1,4]benzodiazepin-5-one
8. 7-Methoxy-8-[N-(1"-pyrenyl)-butane-4'-carboxamide]-oxy-(4R)-hydroxy (11aS)-1,2,3,11a-tetra-hydro-5H-pyrrolo[2,1-c][1,4]benzodiazepin-5-one The process for the preparation of new pyrrolo[2,1-c][1,4]benzodiazepine hybrids is disclosed and claimed in our copending copatent application Ser. No. 10/396,103.

The following examples are given by way of illustration and therefore should not be construed to the present limit of the scope of invention.

EXAMPLE 1

Compound (2S)-N-[4-[(1'-carboxymethyl)oxy]-5-methoxy-2-nitrobenzoyl]pyrrolidine-2-carboxaldehyde diethyl thioacetal of formula II (2.29 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene of formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (2S)-N-{4-[N-(1"-pyrenyl)-methane-3'-carboxamide]-oxy-5-methoxy-2-nitrobenzoyl}pyrrolidine-2-carboxaldehyde diethyl thioacetal of formula III as a yellow liquid.

The (2S)-N-{4-[N-(1"-pyrenyl)-methane-1'-carboxamide]-oxy-5-methoxy-2-nitrobenzoyl}pyrrolidine-2-carboxaldehyde diethyl thioacetal of formula III (0.657 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude (2S)-N-{4-[N-(1"-pyrenyl)-methane-1'-carboxamide]-oxy-5-methoxy-2-aminobenzoyl}pyrrolidine-2-carboxaldehyde diethyl thioacetal of formula IV.

A solution of (2S)-N-{4-[N-(1"-pyrenyl)-methane-1'-carboxamide]-oxy-5-methoxy-2-aminobenzoyl}pyrrolidine-2-carboxaldehyde diethyl thioacetal of formula IV (627 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-propane-3'-carboxamide]-oxy-(11aS)-1,2,3,11a tetra-hydro-5H-pyrrolo[2,1][1,4]benzo-diazepin-5-one as pale yellow oil.

EXAMPLE 2

Compound (4R)-hydroxy-(2S)-N-[4-[(1'-carboxymethyl)oxy]-5-methoxy-2-nitro-benzoyl]pyrrolidine-2-carboxaldehyde diethyl thioacetal of formula II (2.37 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (2S)-N-{4-[N-(1"-pyrenyl)-methane-1'-carboxamide]-oxy-5-methoxy-2-nitrobenzoyl}pyrrolidine-2-carboxaldehyde diethyl thioacetal of formula III as a yellow liquid.

The (4R)-hydroxy-(2S)-N-{4-[N-(1"-pyrenyl)-methane-1'-carboxamide]-oxy-5-methoxy-2-nitrobenzoyl}pyrrolidine-2-carboxaldehyde diethyl thioacetal of formula III (0.673 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude (4R)-hydroxy-(2S)-N-{4-[N-(1"-pyrenyl)-methane-1'-carboxamide]-oxy-5-methoxy-2-amino-benzoyl}pyrrolidine-2-carboxaldehyde diethyl thioacetal of formula IV.

A solution of (4R)-hydroxy-(2S)-N-{4-[N-(1"-pyrenyl)-methane-1'-carboxamide]-oxy-5-methoxy-2-nitrobenzoyl}pyrrolidine-2-carboxaldehyde diethyl thioacetal of formula IV (643 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-methoxy-8-[N-(1"-pyrenyl)-methane-1'-carboxamide]-oxy-(4R)-hydroxy-(11aS)-1,2,3,11a tetra-hydro-5H-pyrrolo[2,1-c][1,4]benzodiazepin-5-one as pale yellow oil.

EXAMPLE 3

Compound (2S)-N-[4-[(2'-carboxyethyl)oxy]-5-methoxy-2-nitrobenzoyl]pyrrolidine-2-carboxaldehyde diethyl thioacetal of formula II (2.36 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene of formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (2S)-N-{4-[N-(1"-pyrenyl)-ethane-2'-carboxamide]-oxy-5-methoxy-2-nitrobenzoyl}pyrrolidine-2-carboxaldehyde diethyl thioacetal of formula III as a yellow liquid.

The (2S)-N-{4-[N-(1"-pyrenyl)-ethane-2'-carboxamide]-oxy-5-methoxy-2-nitrobenzoyl}pyrrolidine-2-carboxaldehyde diethyl thioacetal of formula III (0.671 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude (2S)-N-{4-[N-(1"-pyrenyl)-ethane-2'-carboxamide]-oxy-5-methoxy-2-aminobenzoyl}pyrrolidine-2-carboxaldehyde diethyl thioacetal of formula IV.

A solution of (2S)-N-{4-[N-(1"-pyrenyl)-ethane-2'-carboxamide]-oxy-5-methoxy-2-aminobenzoyl}pyrrolidine-2-carboxaldehyde diethyl thioacetal of formula IV (641 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-ethane-2'-carboxamide]-oxy-(11aS)-1,2,3,11a tetra-hydro-5H-pyrrolo[2,1-c][1,4]benzodiazepin-5-one as pale yellow oil.

EXAMPLE 4

Compound (4R)-hydroxy-(2S)-N-[4-[(2'-carboxyethyl)oxy]-5-methoxy-2-nitrobenzoyl]pyrrolidine-2-carboxaldehyde diethyl thioacetal of formula II (2.44 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene of formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (4R)-hydroxy-(2S)-N-{4-[N-(1"-pyrenyl)-ethane-2'-carboxamide]-oxy-5-methoxy-2-nitrobenzoyl}pyrrolidine-2-carboxaldehyde diethyl thioacetal of formula III as a yellow liquid.

The (4R)-hydroxy-(2S)-N-{4-[N-(1"-pyrenyl)-ethane-2'-carboxamide]-oxy-5-methoxy-2-nitrobenzoyl}pyrrolidine-2-carboxaldehyde diethyl thioacetal of formula III (0.687 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude (4R)-hydroxy-(2S)-N-{4-[N-(1"-pyrenyl)-ethane-2'-carboxamide]-oxy-5-methoxy-2-aminobenzoyl}pyrrolidine-2-carboxaldehyde diethyl thioacetal of formula IV.

A solution of (4R)-hydroxy-(2S)-N-{4-[N-(1"-pyrenyl)-ethane-2'-carboxamide]-oxy-5-methoxy-2-aminobenzoyl}pyrrolidine-2-carboxaldehyde diethyl thioacetal of formula IV (657 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-ethane-2'-carboxamide]-oxy-(4R)-hydroxy-(11aS)-1,2,3,11a tetra-hydro-5H-pyrrolo[2,1-c][1,4]benzodiazepin-5-one as pale yellow oil.

EXAMPLE 5

Compound (2S)-N-[4-[(3'-carboxypropyl)oxy]-5-methoxy-2-nitrobenzoyl]pyrrolidine-2-carboxaldehyde diethyl thioacetal of formula II (2.43 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (2S)-N-{4-[N-(1"-pyrenyl)-propane-3'-carboxamide]-oxy-5-methoxy-2-nitrobenzoyl}pyrrolidine-2-carboxaldehyde diethyl thioacetal of formula III as yellow liquid (1.92 g, 56%).

$^1$H NMR ($CDCl_3$) δ 1.10–1.40 (m, 6H), 1.40–2.40 (m, 6H), 2.50–2.90 (m, 4H), 3.10–3.25 (m, 2H), 3.60 (s, 3H), 4.0–4.20 (m, 2H), 4.55–4.85 (m, 2H), 6.70 (s, 1H), 7.62 (s, 1H), 7.70–8.40 (m, 9H), 8.60–8.90 (m, 1H); MS (FAB) 686 $[M+H]^+$.

The (2S)-N-{4-[N-(1"-pyrenyl)-propane-3'-carboxamide]-oxy-5-methoxy-2-nitrobenzoyl}pyrrolidine-2-carboxaldehyde diethyl thioacetal of formula III (0.685 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude (2S)-N-{4-[N-(1"-pyrenyl)-propane-3'-carboxamide]-oxy-5-methoxy-2-aminobenzoyl}pyrrolidine-2-carboxaldehyde diethyl thioacetal of formula IV (458 mg, 70%).

$^1$H NMR ($CDCl_3$) δ 1.10–1.40 (m, 6H), 1.50–2.30 (m, 8H), 2.40–2.80 (m, 4H), 3.40 (s, 3H), 3.45–3.60 (m, 2H), 4.05–4.15 (m, 2H), 4.50–4.70 (m, 2H), 6.25 (s, 1H), 6.70 (s, 1H), 7.65–8.30 (m, 9H), 9.10–9.25 (m, 1H).

A solution of (2S)-N-{4-[N-(1"-pyrenyl)-propane-3'-carboxamide]-oxy-5-methoxy-2-aminobenzoyl}pyrrolidine-2-carboxaldehyde diethyl thioacetal of formula IV (655 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-propane-3'-carboxamide]-oxy-(11aS)-1,2,3,11a tetra-hydro-5H-pyrrolo[2,1-c][1,4]benzodiazepin-5-one as pale yellow oil of formula V (285 mg, 54%). $^1$H NMR ($CDCl_3$) δ 1.40–2.40 (m, 10H), 2.60–2.90 (m, 2H), 3.40–4.05 (m, 4H), 4.10–4.40 (m, 2H), 6.85 (s, 1H), 7.40 (s, 1H), 7.65 (d, 1H), 7.75–8.20 (m, 8H), 8.20–8.40 (m, 1H), 9.0–9.10 (m, 1H); MS (FAB) 530 $[M+H]^+$.

EXAMPLE 6

Compound (4R)-hydroxy-(2S)-N-[4-[(3'-carboxyethyl)oxy]-5-methoxy-2-nitrobenzoyl]pyrrolidine-2-carboxaldehyde diethyl thioacetal of formula II (2.51 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene of formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (4R)-hydroxy-(2S)-N-{4-[N-(1"-pyrenyl)-ethane-3'-carboxamide]-oxy-5-methoxy-2-nitrobenzoyl}pyrrolidine-2-carboxaldehyde diethyl thioacetal of formula III as a yellow liquid.

The (4R)-hydroxy-(2S)-N-{4-[N-(1"-pyrenyl)-propane-3'-carboxamide]-oxy-5-methoxy-2-nitrobenzoyl}pyrrolidine-2-carboxaldehyde diethyl thioacetal of formula III (0.701 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude (4R)-hydroxy-(2S)-N-{4-[N-(1"-pyrenyl)-propane-3'-carboxamide]-oxy-5-methoxy-2-aminobenzoyl}pyrrolidine-2-carboxaldehyde diethyl thioacetal of formula IV.

A solution of (4R)-hydroxy-(2S)-N-{4-[N-(1"-pyrenyl)-propane-3'-carboxamide]-oxy-5-methoxy-2-aminobenzoyl}pyrrolidine-2-carboxaldehyde diethyl thioacetal of formula IV (671 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-propane-3'-carboxamide]-oxy-(4R) hydroxy-(11aS)-1,2,3,11a tetra-hydro-5H-pyrrolo[2,1-c][1,4]benzodiazepin-5-one as pale yellow oil formula V.

EXAMPLE 7

Compound (2S)-N-{4-[(3'-carboxybutyl)oxy]-5-methoxy-2-nitrobenzoyl}pyrrolidine-2-car-boxaldehyde diethyl thioacetal of formula II (2.50 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (2S)-N-{4-[N-(1"-pyrenyl)-butane-3'-carboxamide]-oxy-5-methoxy-2-nitrobe-nzoyl}pyrrolidine-2-carboxaldehyde diethyl thioacetal of formula III as yellow liquid (1.92 g, 55%).

$^1$H NMR ($CDCl_3$) δ 1.10–1.40 (m, 6H), 1.40–2.40 (m, 8H), 2.50–2.90 (m, 4H), 3.10–3.25 (m, 2H), 3.60 (s, 3H), 4.0–4.20 (m, 2H), 4.55–4.85 (m, 2H), 6.70 (s, 1H), 7.62 (s, 1H), 7.70–8.40 (m, 9H), 8.60–8.90 (m, 1H); MS (FAB) 700 $[M+H]^+$.

The nitro diethyl thioacetal (2S)-N-{4-[N-(1"-pyrenyl)-butane-3'-carboxamide]-oxy-5-methoxy-2-nitrobenzo-yl}pyrrolidine-2-carboxaldehyde diethyl thioacetal of formula III (0.699 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude amino diethyl thioacetal (2S)-N-{4-[N-(1"-pyrenyl)-butane-3'-carboxamide]-oxy-5-methoxy-2-aminobenzoyl}pyrrolidine-2-carboxaldehyde diethyl thioacetal of formula IV (482 mg, 72%).

$^1$H NMR ($CDCl_3$) δ 1.10–1.40 (m, 6H), 1.50–2.30 (m, 10H), 2.40–2.80 (m, 6H), 3.40 (s, 3H), 3.45–3.60 (m, 2H), 4.05–4.15 (m, 2H), 4.50–4.70 (m, 2H), 6.25 (s, 1H), 6.70 (s, 1H), 7.65–8.30 (m, 9H), 9.10–9.25 (m, 1H).

A solution of (2S)-N-{4-[N-(1"-pyrenyl)-butane-3'-carboxamide]-oxy-5-methoxy-2-aminobenzoyl}pyrrolidine-2-carboxaldehyde diethyl thioacetal of formula IV (669 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. Reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-butane-4'-carboxamide]-oxy-(11aS)-1,2,3,11a-tetra-hydro-5H-pyrrolo[2,1-c][1,4]benzodiazepin-5-one of formula V as pale yellow oil (265 mg, 49%). $^1$H NMR ($CDCl_3$) δ 1.40–2.40 (m, 12H), 2.60–2.90 (m, 2H), 3.40–4.05 (m, 4H), 4.10–4.40 (m, 2H), 6.85 (s, 1H), 7.40 (s, 1H), 7.65 (d, 1H), 7.75–8.20 (m, 8H), 8.20–8.40 (m, 1H), 9.0–9.10 (m, 1H); MS (FAB) 544 $[M+H]^+$.

EXAMPLE 8

Compound (4R)-hydroxy-(2S)-N-{4-[(3'-carboxybutyl)oxy]-5-methoxy-2-nitrobenzoyl}pyrrolidine-2-car-boxaldehyde diethyl thioacetal of formula II (2.58 g, 5 mmol) was taken in dry $CH_2Cl_2$ (20 mL), TEA (707 mg, 7 mmol) was added and the mixture was cooled at 0–5° C. Isobutyl chloroformate (819 mg, 6 mmol) in dry $CH_2Cl_2$ (10 mL) was added dropwise and the mixture was kept at 0–5° C. for 15 min. A solution of 1-amino pyrene of formula I (251 mg, 5 mmol) in $CH_2Cl_2$ was added to it at the same temperature and the solution was stirred at room temperature for overnight. The mixture was washed with saturated $NaHCO_3$ (50 mL), brine, dried and solvent was evaporated. The crude material was chromatographed over silica gel using ethyl acetate/hexane (8:2) solvent to give compound (4R)-hydroxy-(2S)-N-{4-[N-(1"-pyrenyl)-butane-3'-carboxamide]-oxy-5-methoxy-2-nitrobe-nzoyl}pyrrolidine-2-carboxaldehyde diethyl thioacetal of formula III as a yellow liquid.

The nitro diethyl thioacetal (4R)-hydroxy-(2S)-N-{4-[N-(1"-pyrenyl)-butane-3'-carboxamide]-oxy-5-methoxy-2-nitrobenzo-yl}pyrrolidine-2-carboxaldehyde diethyl thioacetal of formula III (0.715 g, 1 mmol) was dissolved in ethyl acetate (15 mL) and added $SnCl_2.2H_2O$ (1.12 g, 5 mmol) was refluxed for 3 h or until the TLC indicated that reaction was completed. The reaction mixture was then adjusted to pH 8 carefully with saturated $NaHCO_3$ solution, diluted with ethyl acetate, filtered through celite and extracted. The combined organic phase was dried over $Na_2SO_4$, and evaporated under vacuum to afford the crude amino diethyl thioacetal ((4R)-hydroxy-(2S)-N-{4-[N-(1"-pyrenyl)-butane-3'-carboxamide]-oxy-5-methoxy-2-aminobenzoyl}pyrrolidine-2-carboxaldehyde diethyl thioacetal of formula IV.

A solution of (4R)-hydroxy-(2S)-N-{4-[N-(1"-pyrenyl)-butane-3'-carboxamide]-oxy-5-methoxy-2-aminobenzoyl}pyrrolidine-2-carboxaldehyde diethyl thioacetal of formula IV (681 mg, 1 mmol), $HgCl_2$ (613 mg, 2.26 mmol) and $CaCO_3$ (246 mg, 2.46 mmol) in MeCN-water (4:1) was stirred slowly at room temperature until TLC indicates complete loss of starting material. The reaction mixture was diluted with EtOAc (30 mL) and filtered through a celite bed. The clear yellow organic supernatant was extracted with saturated 5% $NaHCO_3$ (20 mL), brine (20 mL) and the combined organic phase is dried ($Na_2SO_4$). The organic layer was evaporated in vacuum and purified by column chromatography (90% $CH_2Cl_2$—MeOH) to give compound 7-Methoxy-8-[N-(1"-pyrenyl)-butane-4'-carboxamide]-oxy-(4R)-hydroxy-(11aS)-1,2,3,11a-tetra-hydro-5H-pyrrolo[2,1-c][1,4]benzodiazepin-5-one as pale yellow oil formula V as pale yellow oil.

Biological Activity

In vitro biological activity studies were carried out at National Cancer Institute (USA).

Cytotoxicity:

Compounds Ve and Vg were evaluated the primary anticancer activity (Table 1) and further Ve have been evaluated in vitro against sixty human tumour cells derived from nine cancer types (leukemia, non-small-cell lung, colon, CNS, melanoma, ovarian, prostate, and breast cancer). For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of $\log_{10}$TGI and $\log_{10}$LC50 as well as $\log_{10}$ GI50 for Ve are listed in Table 2. As demonstrated by mean graph pattern, compound Ve exhibits an interesting profile of activity and selectivity for various cell lines. The mean graph mid point of log10 TGI and $\log_{10}$ LC50 showed similar pattern to the $\log_{10}$ GI50 mean graph mid point.

TABLE 1

In vitro one dose primary anticancer assay[a] pyrene linked PBD hybrid of formula Ve and Vg

| PBD hybrids | Growth percentages | | |
| --- | --- | --- | --- |
| | (Lung) NCI-H460 | (Breast) MCF7 | (CNS) SF-268 |
| Ve | 11 | 31 | 70 |
| Vg | 106 | 72 | 131 |

[a]One dose of Ve and Vg at $10^{-4}$ molar concentration

The novel pyrrolobenzodiazepine hybrid formula VIIa has shown to possess 10 nano molar potency (at the $LC_{50}$ level) against one non-small cell lung cancer (NCI-H226) and one colon cancer (HCC-2998), and 0.1 micro molar potency against leukemia cancer (SR), melanoma cancer (M14), renal cancer (A498) and CNS cancer (SF-539) and also have 10 micro molar potency against two CNS cancer cell lines (SF539, SNB75) and one prostate cancer (DU-145). The LC50 values of nine cancers (average of six to nine cancer cell lines) of compound VIIa listed in Table 3

TABLE 2

$\log_{10}$ GI50 $\log_{10}$ TGI and $\log_{10}$ LC50 mean graphs midpoints (MG_MID) of in vitro cytotoxicity data for the compound Ve against human tumour cell lines.

| Compound | $\log_{10}$ GI50 | $\log_{10}$ TGI | $\log_{10}$ LC50 |
| --- | --- | --- | --- |
| Ve | −7.75 | −6.89 | −4.74 |

TABLE 3

Log LC50 (concentration in mol/L causing 50% lethality) Values for Compounds Ve

| Cancer | Compound Ve |
| --- | --- |
| Leukemia | −4.65 |
| Non-small-cell lung | −4.67 |
| Colon | −5.00 |
| CNS | −5.23 |
| Melanoma | −5.62 |
| Ovarian | >−4.00 |
| Renal | −5.05 |
| Prostate | −5.30 |
| Breast | >−4.00 |

Each cancer type represents the average of six to nine different cancer cell lines.

We claim:

1. A compound of formula V wherein R is H, OH and n is 1–4

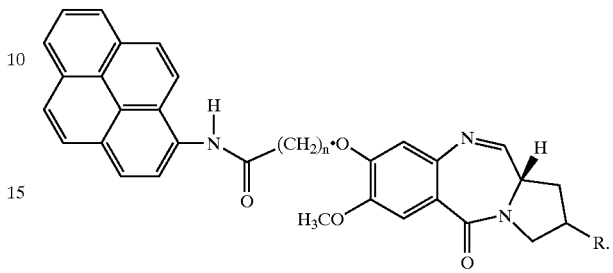

FORMULA V

2. A compound as claimed in claim 1 of the structural formula

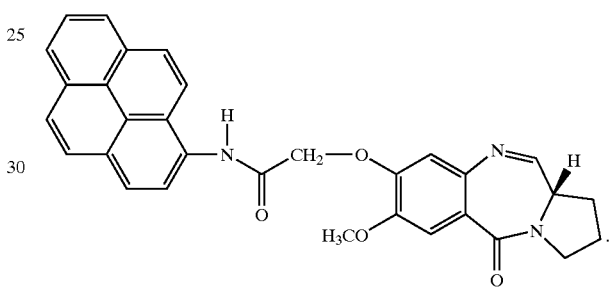

3. A compound as claimed in claim 1 of the structural formula

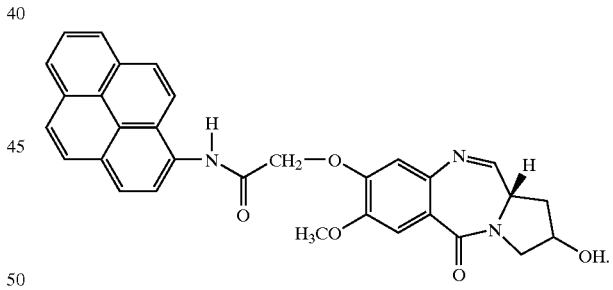

4. A compound as claimed in claim 1 of the structural formula

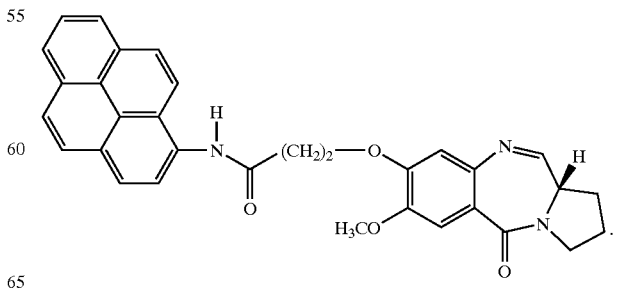

5. A compound as claimed in claim 1 of the structural formula

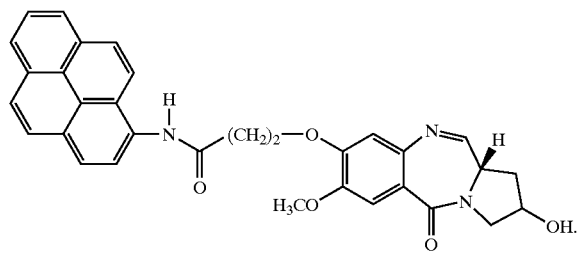

6. A compound as claimed in claim 1 of the structural formula

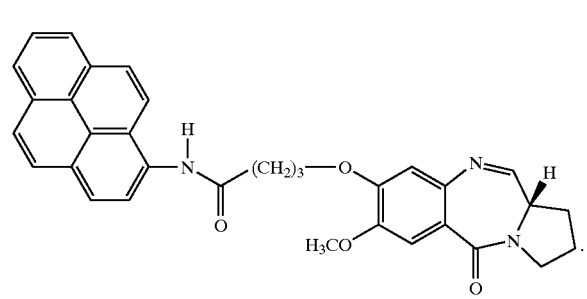

7. A compound as claimed in claim 1 of the structural formula

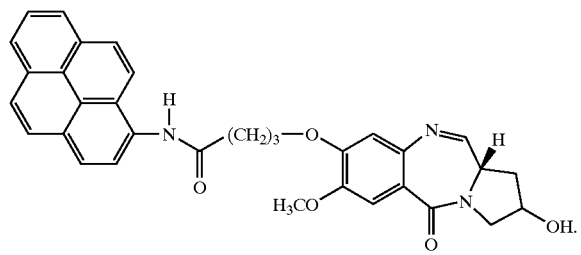

8. A compound as claimed in claim 1 of the structural formula

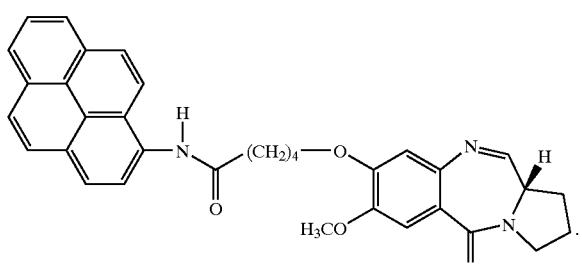

9. A compound as claimed in claim 1 of the structural formula

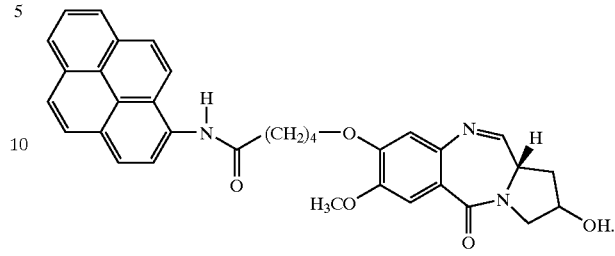

10. A process for preparing a compound of formula V

FORMULA V

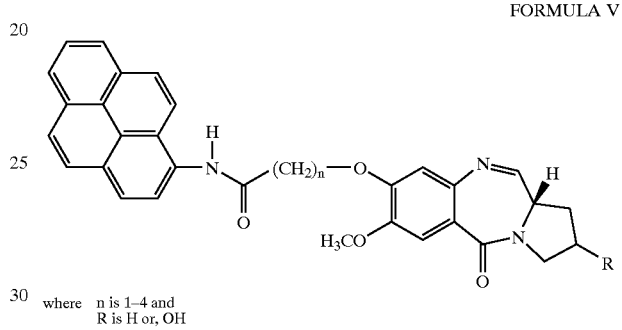

where n is 1–4 and
R is H or, OH which comprises reacting pyrene amine of formula I

I

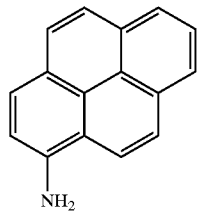

with (2S)-N-{4-[(3'-carboxy alkyl)oxy]-5-methoxy-2-nitrobenzoyl}pyrrolidine-2-carboxyaldehyde diethyl thioacetal of formula II where R is as defined above;

II

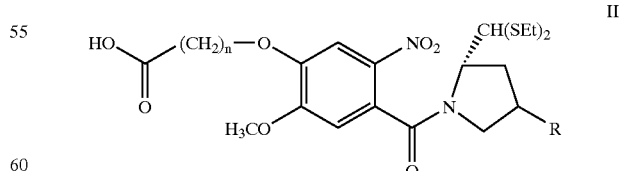

isolating (2S)-N-{4-[N-(1"-pyrenyl)-alkane-3'-carboxamide]-oxy-5-methoxy-2-nitrobenzoyl}pyrrolidine-2-carboxaldehyde diethyl thioacetal III where n is 1–4 and R is as defined above,

III

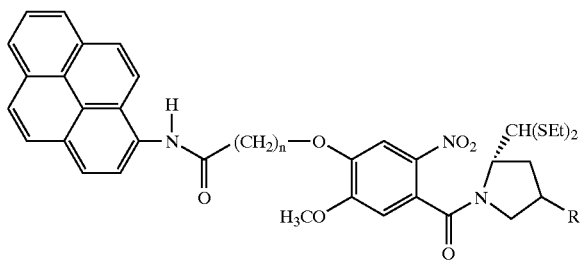

reducing the nitro compound of formula III with SnCl₂.2H₂O in the presence of an organic solvent up to a reflux temperature, isolating the (2S)-N-{4-[N-(1"-pyrenyl)-alkane-3'-carboxamide]-oxy-5-methoxy-2-aminobenzoyl}pyrrolidine-2-carboxaldeyde diethyl thioacetal of formula IV where n is 1–4 and R is as defined above,

IV

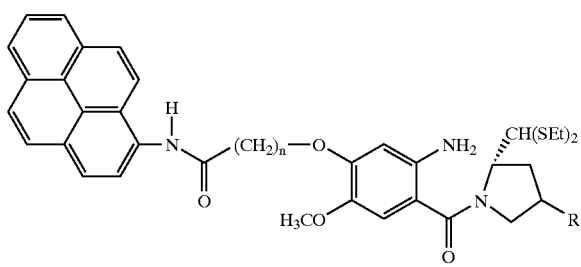

and reacting the amino compound of formula IV with a deprotecting agent to obtain pyrrolo [2,1-c][1,4] benzodiazepine hybrids of formula V wherein n and R are as stated above.

11. A process as claimed in claim 10 wherein the reaction between the compound of formula I and the compound of formula II is carried out in the presence of isobutyl chloroformate and in the presence of a base selected from the group consisting of triethyl amine and DBU; and in the presence of an organic solvent selected from the group consisting of ethyl acetate, hexane and dichloromethane.

12. The process as claimed in claim 10 wherein the organic solvent used for the reduction of the nitro compound of formula III comprises ethyl acetate.

13. A method for the treatment of cancer comprising administering to a subject suffering therefrom, a therapeutically effective amount of a compound of formula V wherein R is H, or OH and n is 1–4 wherein the cancer to be treated is leukemia, non-small-cell lung, colon, CNS, melanoma, ovarian, prostate, or breast cancer

FORMULA V

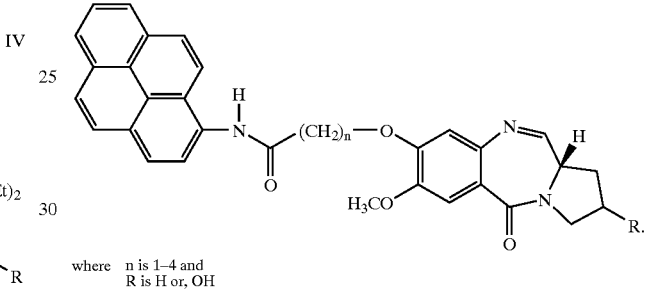

where n is 1–4 and
R is H or, OH

\* \* \* \* \*